US012564567B2

(12) United States Patent
Faulkner et al.

(10) Patent No.: US 12,564,567 B2
(45) **Date of Patent: *Mar. 3, 2026**

(54) ANTIVIRAL THERAPEUTIC COMPOUNDS AND COMPOSITIONS FOR USE IN TREATMENT OF CORONAVIRUS AND INFLUENZA VIRUS

(71) Applicant: Vireo Systems, Inc., Madison, TN (US)

(72) Inventors: Mark C. Faulkner, Madison, TN (US); Donald W. Miller, Winnipeg (CA)

(73) Assignee: Vireo Systems, Inc., Madison, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/519,436

(22) Filed: Nov. 27, 2023

(65) Prior Publication Data

US 2024/0165067 A1 May 23, 2024

Related U.S. Application Data

(63) Continuation of application No. 17/533,528, filed on Nov. 23, 2021, now Pat. No. 11,826,334.

(60) Provisional application No. 63/116,977, filed on Nov. 23, 2020.

(51) Int. Cl.

| | |
|---|---|
| ***A61K 31/215*** | (2006.01) |
| ***A61K 45/06*** | (2006.01) |
| ***A61P 31/12*** | (2006.01) |

(52) U.S. Cl.

CPC ............ *A61K 31/215* (2013.01); *A61K 45/06* (2013.01); *A61P 31/12* (2018.01)

(58) Field of Classification Search

CPC .............................. A61K 31/215; A61P 31/12

See application file for complete search history.

(56) References Cited

U.S. PATENT DOCUMENTS

| | | | |
|---|---|---|---|
| 8,354,450 | B2 | 1/2013 | Miller et al. |
| 2007/0203076 | A1 | 8/2007 | Vennerstrom et al. |
| 2015/0164847 | A1 | 6/2015 | Faulkner et al. |
| 2019/0247354 | A1 | 8/2019 | Miller et al. |

FOREIGN PATENT DOCUMENTS

| | | | |
|---|---|---|---|
| RU | 2579120 | * | 3/2016 |
| WO | 93/12781 | | 7/1993 |
| WO | 2012/054701 | | 4/2012 |
| WO | 2016/172148 | | 10/2016 |
| WO | 2020223608 | | 11/2020 |

OTHER PUBLICATIONS

Grau et al., Neurology 1998, 50, 196-203.*

Greenhaff, Paul L., "The nutritional biochemistry of creatine", J. Nutr. Biochem., vol. 8, pp. 610-618 (1997).

Williams, Melvin H., et al., "Creatine Supplementation and Exercise Performance: An Update", Journal of the American College of Nutrition, vol. 17, No. 3, pp. 216-234 (1998).

Riesberg, L.A. et al., Creatinine downregulates TNF-a in macrophage and T cell lines, Cytokine, 2018, vol. 110, pp. 29-38.

Leland, K.M. et al., Effect of creatine, creatinine, and creatine ethyl ester on TLR expression in macrophages, International Immunopharmacollogy, May 14, 2011 (online publication date), vol. 11, pp. 1341-1347.

Di Biase, S. et al., Creatine uptake regulates CD8 T cell antitumor immunity, Journal of Experimental Medicine, Dec. 2, 2019, vol. 216, Issue 12, pp. 2869-2882.

Riesberg, L.A. et al., Beyond muscles: The untapped potential of creatine, International Immunopharmacology, 2016, vol. 37, pp. 31-42.

International Search Report and Written Opinion dated Mar. 15, 2022 of corresponding International Patent Application No. PCT/US2021/060546.

Alraddadi et al., The Canadian Journal of Veterinary Research, 2019, pp. 206-2017.

The Science and Practice of Pharmacy, Nineteenth Edition—1995, pp. 710-712; pp. 1524-1528.

Gufford, Brandon et al., J Diet Suppl, Sep. 2013; 10(3): 241-251.

Ostojic, Sergei M., "Can Creatine Help in Pulmonary Rehabilitation After COVID-19?", Therapeutic Advances in Respiratory Disease, Jan. 1, 2020, vol. 14, pp. 1-2.

Extended European Search Report dated Sep. 13, 2024 of corresponding European Patent Application No. 21895810.6.

* cited by examiner

*Primary Examiner* — Shobha Kantamneni

(74) *Attorney, Agent, or Firm* — Bradley Arant Boult Cummings LLP

(57) ABSTRACT

Antiviral therapeutic compounds and compositions that may be used in methods of preventing and/or treating infection(s) caused by coronaviruses or influenza viruses.

22 Claims, 4 Drawing Sheets

ANTIVIRAL THERAPEUTIC COMPOUNDS AND COMPOSITIONS FOR USE IN TREATMENT OF CORONAVIRUS AND INFLUENZA VIRUS

FIELD OF THE INVENTION

The present invention relates to antiviral therapeutic compounds and related for their use in compositions for the treatment and/or the prevention of infection(s) caused by coronaviruses or influenza viruses. More specifically, the present invention generally relates to antiviral therapeutic compounds and related compositions useful in the treatment and/or general support during treatment of coronavirus infection or infection with the influenza virus. The antiviral therapeutic compounds are also useful prophylactically to strengthen or boost the immune system to allow the body to prevent infection caused by coronaviruses or influenza viruses.

BACKGROUND OF THE INVENTION

Amino acids and modified amino acids have been of interest in the context of dietary supplements. In particular, betaine and creatine are generally recognized as safe and well-tolerated for use in dietary supplementation, mostly for weight loss and muscle recovery. Some of these amino acids and modified amino acids have critical roles in energy production/homeostasis; others have ancillary roles. For example, betaine (trimethylglycine) is a modified amino acid consisting of glycine with three methyl groups. Betaine is involved in liver function, cellular reproduction, and helping make carnitine. As such, it has at least an indirect role in cellular energy production. Betaine also metabolizes homocysteine and, thus, prevents its build-up in the body, which can harm blood vessels and contribute to heart disease, stroke, or circulation problems.

Creatine, which is an organic acid that is synthesized in the liver and kidneys from three amino acids: arginine, glycine, and methionine, plays a pivotal role in cellular energy homeostasis (Greenhaff P, J Nutr Biochem 8: 610-618 (1997); Williams MH et al., J Am Coll Nutr 17: 216-234 (1998)). In particular, homeostasis requires a balance between adenosine triphosphate (ATP) production (metabolism) and ATP consumption (synaptic activity). When ATP is transferring energy to cells, it breaks off one of its phosphates and becomes adenosine diphosphate (ADP). In the muscle, creatine converts into phosphocreatine by creatine kinase, which is utilized to increase the ATP pool during excess energy use. More specifically, the phosphocreatine donates a phosphate to the ADP and turns it back into ATP to once more be utilized as cellular energy. Thus, the more creatine in the system, the more ADP that can be recycled back into ATP, and the larger cellular reserve of ATP available to the cell for carrying out its functions.

The body is normally capable of producing enough of each of creatine and betaine to meets its metabolic needs under usual conditions. However, during times of physiologically stressful conditions such as stress, illness or disease, and/or excess exercise, the biosynthesis of each or all of these nutrients may be inadequate. In other words, under certain conditions, the requirements for these conditionally essential nutrients may exceed the body's capacity to synthesize each of these nutrients.

One such condition is the infection with a virus. For example, coronaviruses are a family of viruses that, depending on the specific genomic sequence of the strain, cause illnesses ranging from the common cold, severe acute respiratory syndrome (SARS), Middle East respiratory syndrome (MERS), and severe acute respiratory syndrome coronavirus 2 (SARS-COV-2). The viral S (spike) proteins on the surface of the coronavirus have spike-like structures that allows them to attach to the surface of human cells. As recently experienced, SARS-COV-2, which is the strain of coronavirus that causes coronavirus disease 2019 (COVID-19), is more contagious and appears to have a higher fatality rate than previous coronavirus strains. In fact, research has shown that SARS-COV-2 binds 10 times more tightly to host cells than SARS-COV. Some studies suggest that this is partly due to the fact that, unlike SARS-COV and other coronaviruses in the family, the S protein on SARS-COV-2 contains a site that recognizes and becomes activated by an enzyme called furin. Furin is a host-cell enzyme in a number of human organs, e.g., the liver, the lungs, and the small intestines, and, since this enzyme resides in so many of these human tissues, SARS-COV-2 can potentially attack several organs at once. In SARS-COV-2 infection, the spike protein receptor-binding domain binds to the angiotensin-converting enzyme 2 (ACE2). Typically, the membrane-bound full-length ACE2 functions to protect against organ injury by cleavage and disposal of Angiotensin II, formation of Angiotensin 1-7, and degradation of des-arg BK 1-8. However, in SARS-COV-2 infection, the host cell proteases then cleave the SARS-COV-2 spike protein for successful entry into the cell and the circulating soluble ACE2 protein (unlike the membrane-bound full-length ACE2) is not able to enter the cell since it now lacks the transmembrane domain. A lack of ACE2 could lead to accumulation of BK (1-8) and an excessive level of proinflammatory peptides in the lungs.

Since inflammation is one of the most complicating and health-compromising aspects of coronavirus and influenza virus and hyper-inflammation may lead to exacerbated recovery and/or death, it would be advantageous to identify compounds and compositions that help to reduce the host cell inflammatory response in patients infected with coronaviruses and influenza viruses. In addition, it would be beneficial to identify compounds and compositions that help to reduce the expression of proinflammatory cytokines and chemokines that contribute to the process of inflammation when exposed to viral proteins. Moreover, it would be advantageous to identify compounds and compositions that provide increased immune support for patients infected with coronaviruses, including SARS-COV-2, as well as influenza viruses. In this aspect, it would be beneficial to identify compounds and compositions that help to increase interferon gamma release in T cells when challenged with a virus. It would also be beneficial to use such compounds and compositions in a prophylactic manner. The present invention provides such antiviral therapeutic compounds and compositions.

SUMMARY OF THE INVENTION

The present invention is related to antiviral therapeutic compounds and compositions effective in preventing, treating, and/or enhancing or supporting the treatment of infection with coronavirus. In one embodiment, a composition having at least one of the following antiviral therapeutic compounds is administered to a patient infected with coronavirus:

A

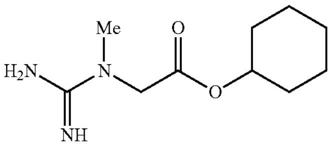

A

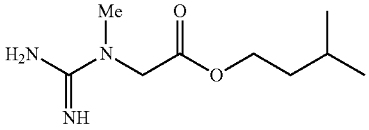

A

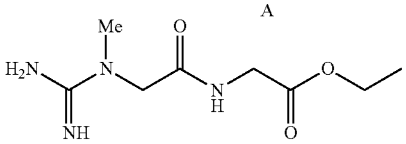

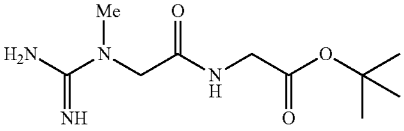

A

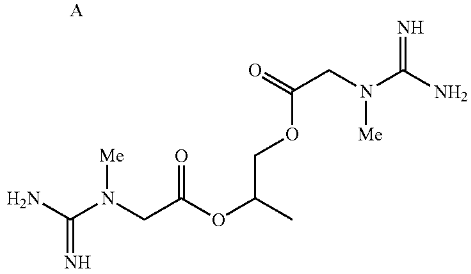

A A

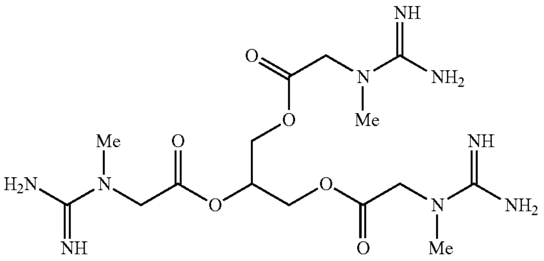

A A A

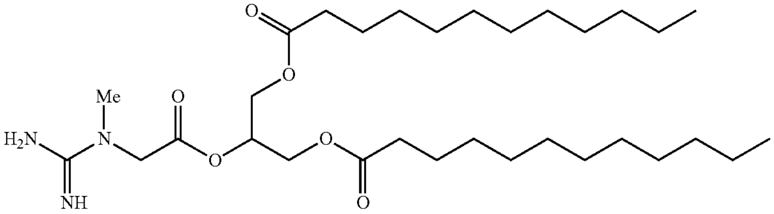

A

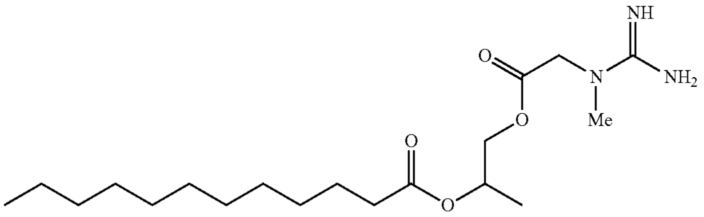

A where A is a salt. In one embodiment, A is chloride, bromide, sulfate, or phosphate. In another embodiment, A is hydrogen chloride, hydrogen bromide, hydrogen sulfate, or hydrogen phosphate. In another embodiment, a composition having at least two of the above compounds is administered to a patient infected with coronavirus. The compositions may also be administered to a patient that has not yet been infected.

In another embodiment, a composition having the following antiviral therapeutic compound is administered to a patient infected with coronavirus:

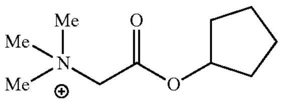

A where A is a salt. In one embodiment, A is chloride, bromide, sulfate, or phosphate. In another embodiment, A is hydrogen chloride, hydrogen bromide, hydrogen sulfate, or hydrogen phosphate. In another embodiment, A is mesylate or tosylate. In yet another embodiment, A is succinate, tartrate, or acetate. The compositions may also be administered to a patient that has not yet been infected.

In another embodiment, a composition having at least one of the following antiviral therapeutic compounds is administered to a patient infected with coronavirus:

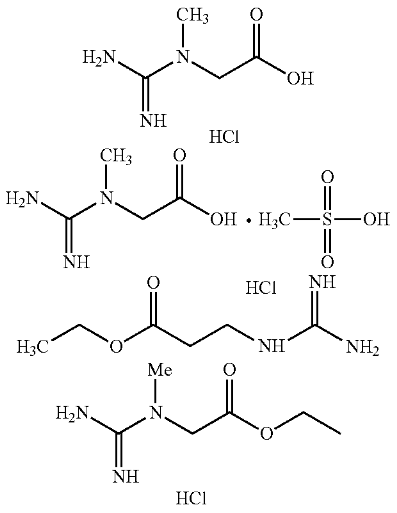

In another embodiment, a composition having at least two of the above compounds is administered to a patient infected with coronavirus. The compositions may also be administered to a patient that has not yet been infected.

The present invention is also directed to a method of treating coronavirus in a patient in need thereof, including administering to the patient an effective amount of a composition comprising at least one antiviral therapeutic compound, wherein the antiviral therapeutic compound comprises creatine cyclohexyl ester, creatine isopentyl ester, or combinations thereof. In one embodiment, the antiviral therapeutic compound is present in the composition in an amount of about 50 percent or greater by weight of the composition. In another embodiment, the antiviral therapeutic compound is present in the composition in an amount of about 60 percent or greater by weight of the composition. The composition may be administered to the patient orally. In the alternative, the composition may be administered intravenously.

The present invention is also related to a method of treating coronavirus in a patient in need thereof, including administering to the patient an effective amount of at least one antiviral therapeutic compound, wherein the antiviral therapeutic compound is selected from the group consisting of creatine hydrochloride, ethyl (α-guanido-methyl) ethanoate, creatine cyclohexyl ester, creatine isopentyl ester, betaine cyclopentyl ester, and combinations thereof. The step of administering may include administering the antiviral therapeutic compound in an amount of about 400 mg/g to about 500 mg/g per dose. In one embodiment, the antiviral therapeutic compound is present in the composition in an amount of about 50 percent or greater by weight of the composition. In another embodiment, the antiviral therapeutic compound is present in the composition in an amount of about 60 percent or greater by weight of the composition. The composition may be administered to the patient orally. In the alternative, the composition may be administered intravenously.

The present invention is also related to a method of treating coronavirus in a patient in need thereof, including administering to the patient an effective amount of a composition including at least one antiviral therapeutic compound and at least one anti-inflammatory agent, wherein the antiviral therapeutic compound includes creatine cyclohexyl ester, creatine isopentyl ester, betaine cyclopentyl ester, or a combination thereof and wherein the anti-inflammatory agent includes ethyl (α-guanido-methyl) ethanoate, wherein the antiviral therapeutic compound is present in the composition in an amount of about 50 percent or greater by weight of the composition. In one embodiment, the composition is administered to the patient orally. In another embodiment, the composition is administered to the patient intravenously. In yet another embodiment, the composition comprises about 400 mg to about 800 mg of the antiviral therapeutic compound per dose and about 300 mg to about 600 mg of the anti-inflammatory agent per dose.

The present invention is also related to antiviral therapeutic compounds and compositions effective in preventing, treating, and/or enhancing or supporting the treatment of patients infected with influenza virus. In one embodiment, a composition having at least one of the following antiviral therapeutic compounds is administered to a patient infected with influenza virus:

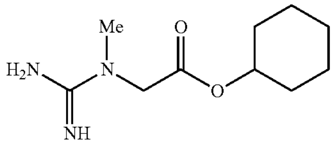

A

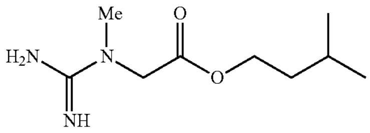

A

A

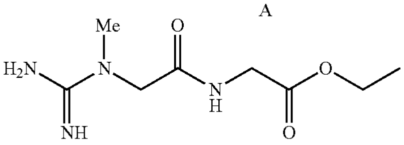

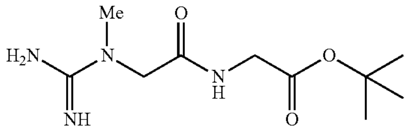

A

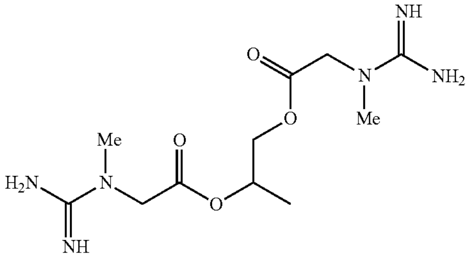

A A

-continued

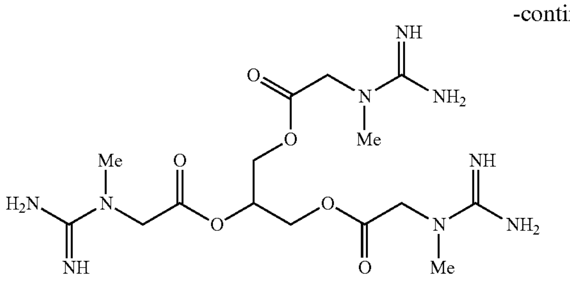

A A A

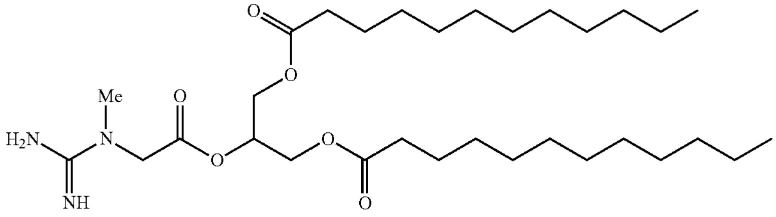

A

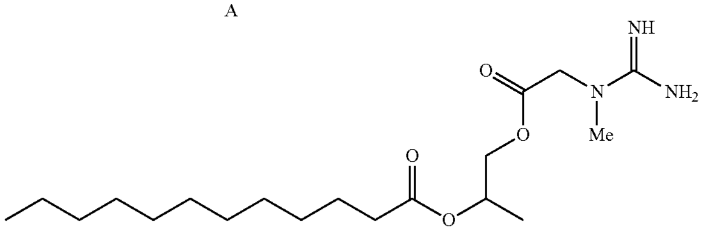

A where A is a salt. In one embodiment, A is chloride, bromide, sulfate, or phosphate. In another embodiment, A is hydrogen chloride, hydrogen bromide, hydrogen sulfate, or hydrogen phosphate. In another embodiment, a composition having at least two of the above compounds is administered to a patient infected with influenza virus. The compositions may also be administered to a patient that has not yet been infected.

In another embodiment, a composition having the following antiviral therapeutic compound is administered to a patient infected with influenza virus:

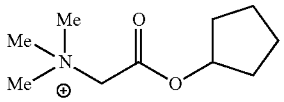

A where A is a salt. In one embodiment, A is chloride, bromide, sulfate, or phosphate. In another embodiment, A is hydrogen chloride, hydrogen bromide, hydrogen sulfate, or hydrogen phosphate. In another embodiment, A is mesylate or tosylate. In yet another embodiment, A is succinate, tartrate, or acetate. The compositions may also be administered to a patient that has not yet been infected.

In another embodiment, a composition having at least one of the following antiviral therapeutic compounds is administered to a patient infected with influenza virus:

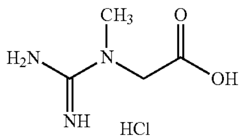

HCl

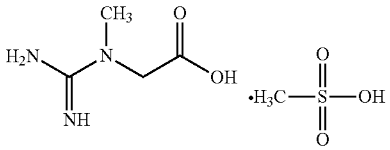

HCl

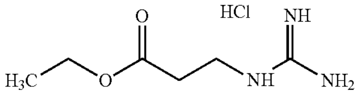

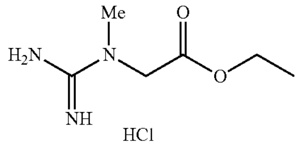

HCl

In another embodiment, a composition having at least two of the above compounds is administered to a patient infected with influenza virus. The compositions may also be administered to a patient that has not yet been infected.

BRIEF DESCRIPTION OF THE DRAWINGS

Further features and advantages can be ascertained from the following detailed description that is provided in connection with the drawings described below.

DETAILED DESCRIPTION OF THE INVENTION

Figure 1:
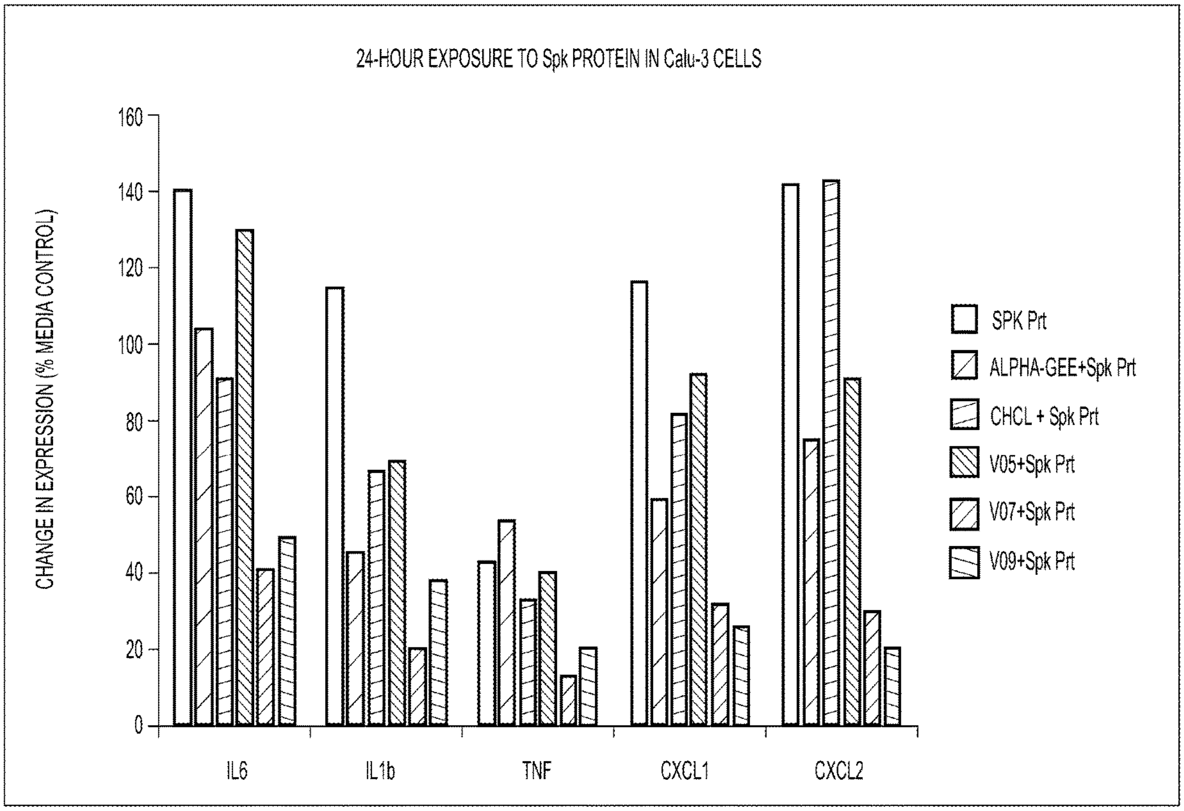
FIG. 1 is a graphical illustration showing the expression of inflammatory genes in response to exposure to SARS- COV-2 spike protein in the presence and absence of certain antiviral therapeutic compounds of the present disclosure.

The present invention is directed to antiviral therapeutic compounds intended to reduce inflammatory responses in, provide immune support to, and increase survival of patients infected with coronavirus or influenza virus. The present invention is also directed to compositions including such antiviral therapeutic compounds and methods of administering compositions including such antiviral therapeutic compounds.

Without being bound to a particular theory, it is contemplated that the increased solubility and/or permeability of the antiviral therapeutic compounds disclosed herein to a patient optimize antiviral therapeutic production and/or homeostasis and, thus, allow the body to more effectively mount an immune defense against the virus. Similarly, the antiviral therapeutic compounds disclosed herein reduce the inflammatory response to the viral proteins. Moreover, administration of compositions including the antiviral therapeutic compounds is believed to generally provide the body with adequate energy to elicit a potent immune defense against the viruses.

Antiviral Therapeutic Compounds

In one embodiment, the antiviral therapeutic compounds of the present invention may be one of the following compounds:

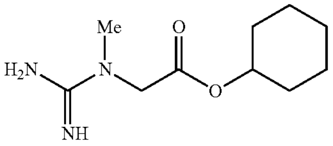

A creatine cyclohexyl ester

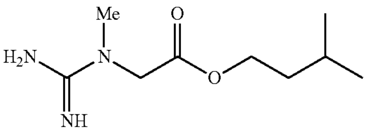

A creatine isopentyl ester

A

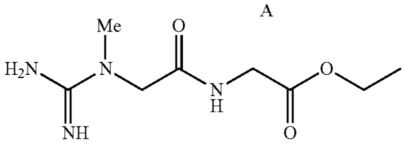

creatine amide ethyl ester

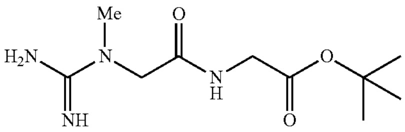

A creatine amide tert butyl ester

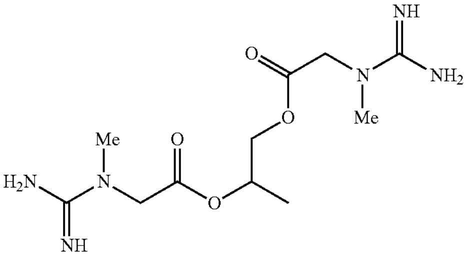

A A dicreatine glycerol ester

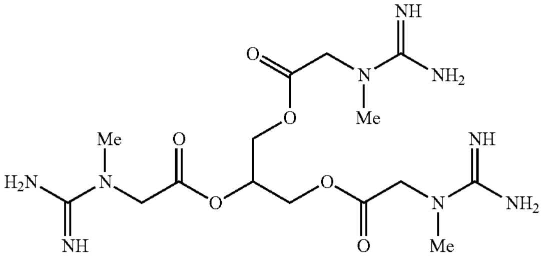

A A A tricreatine glycerol ester

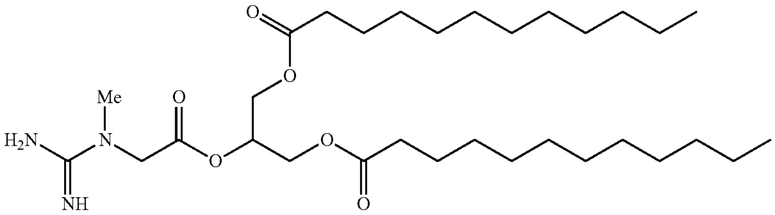

A creatine glycerol laurate ester

-continued

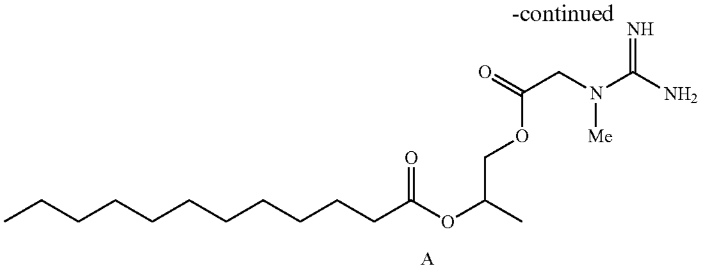

creatine propylene glycol laurate ester where A is a salt. In one embodiment, A is chloride, bromide, sulfate, or phosphate. In another embodiment, A is hydrogen chloride, hydrogen bromide, hydrogen sulfate, or hydrogen phosphate. For example, the antiviral therapeutic compounds may be a creatine isopentyl ester where A is hydrogen chloride as shown below:

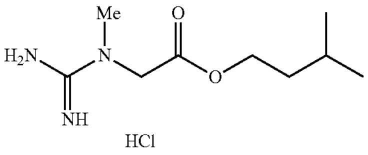

In another embodiment, A is mesylate or tosylate. For example, the antiviral therapeutic compound may be a creatine cyclohexyl ester where A is tosylate as shown in the structure below:

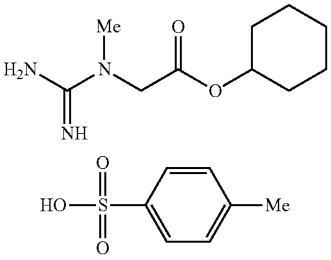

In yet another embodiment, A is succinate, tartrate, or acetate.

In another embodiment, the antiviral therapeutic compound may be a betaine cyclopentyl ester having the following structure:

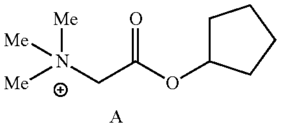

where A is a salt. In one embodiment, A is chloride, bromide, sulfate, or phosphate. For example, in one embodiment, the antiviral therapeutic compound may be a betaine cyclopentyl ester where A is bromide as shown below:

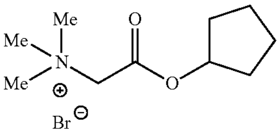

In another embodiment, A is hydrogen chloride, hydrogen bromide, hydrogen sulfate, or hydrogen phosphate. In another embodiment, A is mesylate or tosylate. In yet another embodiment, A is succinate, tartrate, or acetate.

In still another embodiment, the antiviral therapeutic compounds include, but are not limited to, the following compounds:

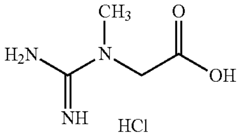

creatine hydrochloride

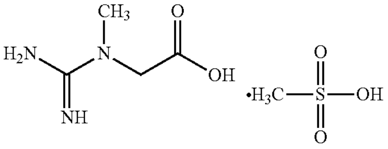

creatine mesylate

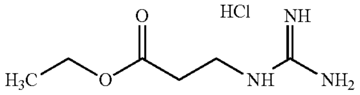

ethyl (α-guanido-methyl) ethanoate

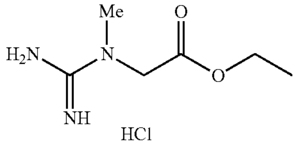

creatine ethyl ester hydrochloride

Solubility/Permeability

Solubility and permeability are two important factors in the amount of an antiviral therapeutic compound made available to an organism, otherwise known as bioavailability. Solubility refers to the amount of the antiviral therapeutic compound that may be dissolved, whereas permeability refers to the ability of the antiviral therapeutic compound to penetrate across a barrier, such as a membrane, cell wall, and the like. Accordingly, many of the antiviral therapeutic compounds of the present invention have (i) high aqueous solubility, (ii) improved cell permeability/penetration, or (iii) both.

In fact, of the antiviral therapeutic compounds disclosed herein, creatine hydrochloride, creatine mesylate, creatine ethyl ester hydrochloride, creatine amide ethyl ester, creatine amide tert butyl ester, and creatine isopentyl ester possess solubility significantly greater than other forms of creatine such as creatine monohydrate. Likewise, betaine cyclopentyl ester has a solubility that is significantly greater than creatine monohydrate. In addition, betaine cyclopentyl ester has a solubility that is significantly greater than betaine hydrochloride.

In this aspect, the antiviral therapeutic compounds of the present invention may have a ratio of solubility (relative to creatine monohydrate) of at least about 5. In one embodiment, the ratio of solubility relative to creatine monohydrate is about 8 or greater. In another embodiment, the antiviral therapeutic compound has a ratio of solubility (relative to creatine monohydrate) of about 15 or greater. In yet another embodiment, the antiviral therapeutic compound has a ratio of solubility (relative to creatine monohydrate) of about 20 or greater. In still another embodiment, the antiviral therapeutic compound has a ratio of solubility (relative to creatine monohydrate) of about 25 or greater.

Likewise, betaine cyclopentyl ester has a ratio of solubility (relative to betaine hydrochloride) of at least about 5. In one embodiment, the ratio of solubility relative to betaine hydrochloride is about 8 or greater. In another embodiment, the antiviral therapeutic compound has a ratio of solubility (relative to betaine hydrochloride) of about 15 or greater. In yet another embodiment, the antiviral therapeutic compound has a ratio of solubility (relative to betaine hydrochloride) of about 20 or greater. In still another embodiment, the antiviral therapeutic compound has a ratio of solubility (relative to betaine hydrochloride) of about 25 or greater.

In one embodiment, the antiviral therapeutic compounds have an aqueous solubility of at least about 200 mg/ml at room temperature (25° C.) after a time period of about 1.5 hours. In another embodiment, the solubility of the antiviral therapeutic compounds is at least about 300 mg/ml at 25° C. after about 1.5 hours. In yet another embodiment, the antiviral therapeutic compounds have an aqueous solubility of at least about 400 mg/ml at 25° C. after about 1.5 hours. In still another embodiment, the antiviral therapeutic compounds may possess an aqueous solubility at room temperature (25° C.) after a time period of about 1.5 hours of about 500 mg/ml or greater, and preferably of about 600 mg/mL or greater.

In another embodiment, the aqueous solubility of the antiviral therapeutic compounds ranges from about 400 mg/ml to about 1000 mg/ml. In yet another embodiment, the antiviral therapeutic compounds have an aqueous solubility of about 500 mg/ml to about 1000 mg/ml. In still another embodiment, the aqueous solubility of the antiviral therapeutic compounds of the invention is at least about 650 mg/ml, preferably at least about 675 mg/ml. In yet another embodiment, the antiviral therapeutic compounds have a solubility of at least about 700 mg/ml or greater at 25° after a time period of about 1.5 hours.

In addition, creatine cyclohexyl ester and the creatine derivatives based on fatty acid esters, propylene glycol, and glycerol laurates have improved cell penetration over that of creatine monohydrate. Without being bound by any particular theory, while these creatine derivatives may not have high aqueous solubility like those in the preceding discussion, each has more lipophilicity for better tissue and cell penetration that is not tied to a creatine transporter. In this aspect, creatine cyclohexyl ester, creatine glycerol laurate ester, creatine propylene glycol laurate ester, and combinations thereof have better cell permeability than creatine monohydrate. More specifically, it is contemplated that laboratory analysis performed in MDCK monolayers show that flux per hour with creatine cyclohexyl ester, creatine glycerol laurate ester, creatine propylene glycol laurate ester, and combinations thereof is at least double that of creatine monohydrate. In other words, if 10% of the original amount of creatine monohydrate added to one side of the MDCK monolayer made it across to the other side in a 60-minute period, about 20% of the original amount of creatine cyclohexyl ester, creatine glycerol laurate ester, creatine propylene glycol laurate ester, or combinations thereof added to one side of the MDCK monolayer will make it across to the other side over the same time period. Similar results are expected in a Caco-2 monolayer, which may be used as an in vitro model for intestinal absorption.

The antiviral therapeutic compounds of the present invention may also have high solubility and improved cell permeability over that of creatine monohydrate. In this aspect, certain antiviral therapeutic compounds disclosed herein have a solubility of at least about 150 mg/ml at 25° C. for a time period of about 1.5 hours and at least a 5-fold greater cell permeability than creatine monohydrate. In another embodiment, the antiviral therapeutic compounds have a solubility of at least about 175 mg/ml at 25° C. for a time period of about 1.5 hours and at least a 10-fold greater cell permeability than creatine monohydrate. In another embodiment, the antiviral therapeutic compounds have a solubility of at least about 200 mg/ml at 25° C. for a time period of about 1.5 hours and at least a 15-fold greater cell permeability than creatine monohydrate. In this aspect, creatine ethyl ester hydrochloride and betaine cyclopentyl ester are examples of antiviral therapeutic compounds that have higher solubility and improved cell permeability in accordance with the present invention. For example, solubility studies have shown that creatine ethyl ester hydrochloride has a solubility of greater than 200 mg/ml at 25° C. after 1.5 hours. In addition, studies have shown that creatine ethyl ester hydrochloride has a 15-fold greater permeability in Caco-2 monolayers than creatine monohydrate (see, e.g., Gufford, Brandon et al., J Diet Suppl. 2013 September; 10(3): 241-251).

Bioavailability

The antiviral therapeutic compounds of the present invention are also expected to have good oral absorption properties. As used herein, the term "bioavailability" refers to the rate and amount of a drug that reaches the systemic circulation of a patient following administration of the substance or form of the substance to the patient. By definition, when a composition is administered intravenously, its bioavailability is 100 percent. However, when a composition is administered via other routes (such as orally), its bioavailability decreases (due to incomplete absorption and first-pass metabolism). More specifically, bioavailability is a measure of the ratio of the amount of substance "absorbed" from a test formulation to the amount "absorbed" after administration of a standard formulation. Frequently, the "standard formulation" used in assessing bioavailability is the aqueous solution of the substance, given intravenously.

Accordingly, bioavailability is one of the principal pharmacokinetic properties of substances and can be determined by evaluating, for example, the plasma or blood concentration-versus-time profile for a substance. Parameters useful in characterizing a plasma or blood concentration-versus-time curve include the area under the curve (AUC), the maximum concentration ($C_{max}$), and the time to maximum concentration ($T_{max}$). As used herein, the term "AUC" refers to the area under a curve representing the concentration of a compound or metabolite thereof in a biological fluid, e.g., plasma and blood, in a patient as a function of time following administration of the antiviral therapeutic compound to the patient. The AUC may be determined by measuring the concentration of a compound or metabolite thereof in a biological fluid using methods such as liquid chromatography-tandem mass spectrometry (LC/MS/MS), at various time intervals, and calculating the area under the plasma concentration-versus-time curve. Suitable methods for calculating the AUC from a concentration-versus-time curve are well known in the art. $C_{max}$ is the maximum concentration of a drug in the plasma or blood of a patient following administration of a dose of the substance or form of the substance to the patient. $T_{max}$ is the time to the maximum concentration ($C_{max}$) of a substance in the plasma or blood of a patient following administration of a dose of the substance or form of the substance to the patient.

The amount of substance absorbed is taken as a measure of the ability of the formulation to deliver the substance to the sites of action. Obviously—depending on such factors as disintegration and dissolution properties of the dosage form, and the rate of biotransformation relative to the rate of absorption—dosage forms containing identical amounts of active substance may differ markedly in their abilities to make the substance available, and therefore, in their abilities to permit the substance to manifest its expected pharmacodynamic and therapeutic properties. The "amount absorbed" is conventionally measured by one of two criteria, either the area under the time-plasma concentration curve (AUC) or the total (cumulative) amount of the substance excreted in the urine following drug administration. A linear relationship exists between the AUC and dose when the fraction of the drug absorbed is independent of dose, and elimination rate (half-life) and volume of distribution are independent of dose and dosage form. However, when AUC is dependent on dose, as occurs when, for example, there is saturable absorption, significant metabolism, or poor solubility of the substance in the GI tract, a non-linear relationship exists between AUC and dose.

In order to compare the relative bioavailability of certain antiviral therapeutic compounds and to correct for the slightly different doses administered with various forms due to the different molecular weights, the AUC plasma uptake values observed for the standard (here, creatine monohydrate) and each antiviral therapeutic creatine compound are entered into the following equation to produce a ratio:

$$\frac{AUC_{SampleA} \times \text{Dose}_B}{AUC_{SampleB} \times \text{Dose}_A}$$

Based on this relationship, the relative bioavailability of any of the antiviral therapeutic creatine compounds to the standard is about 1.3 or greater, preferably about 1.5 or greater, and more preferably about 1.6 or greater. In one embodiment, the ratio is about 1.7 or greater.

In other words, the relative bioavailability of the antiviral therapeutic creatine compounds of the invention is at least about 30 percent greater than creatine monohydrate, preferably about 40 percent greater than creatine monohydrate, and more preferably about 50 percent greater than creatine monohydrate. In one embodiment, the bioavailability of the antiviral therapeutic creatine compounds of the invention is at least about 50 percent greater than bioavailability of creatine monohydrate. In another embodiment, the bioavailability of the antiviral therapeutic creatine compounds of the invention is at least about 65 percent greater than bioavailability of creatine monohydrate. In yet another embodiment, the antiviral therapeutic creatine compounds of the invention have a bioavailability of at least about 70 percent greater relative to creatine monohydrate.

Synthesis

The antiviral therapeutic compounds of the present invention may be synthesized by any suitable method known to one of ordinary skill in the art. For example, in one embodiment, the antiviral therapeutic compound is creatine hydrochloride synthesized from hydrochloric acid (pKa-6) in accordance with any of the methods disclosed in U.S. Pat. No. 8,354,450, the entire disclosure of which is incorporated by reference herein. In another embodiment, the antiviral therapeutic compound is creatine mesylate synthesized from methane sulfonic acid (pKa -1.2). In still another embodiment, the antiviral therapeutic compound is creatine ethyl ester hydrochloride and is synthesized in accordance with the methods described in U.S. Patent Publication No. 2007/0203076, the entire disclosure of which is incorporated by reference herein.

Preparations of the antiviral therapeutic compounds are preferably at least about 80 percent pure, preferably at least about 95 percent pure, more preferably at least about 97 percent pure, and even more preferably at least about 99 percent pure. The term "pure" as used herein refers to the lack of impurities in the preparation.

Composition

The antiviral therapeutic compounds discussed above may be formulated into an antiviral therapeutic composition. In one embodiment, a composition made in accordance with the present invention includes at least one antiviral therapeutic compound disclosed herein. For example, in one embodiment, the antiviral therapeutic composition includes creatine cyclohexyl ester, creatine isopentyl ester, creatine glycerol laurate ester, creatine propylene glycol laurate ester, creatine amide ethyl ester, creatine amide tert butyl ester, dicreatine glycerol ester, tricreatine glycerol ester, betaine cyclopentyl ester, or combinations thereof.

For example, a composition made in accordance with the present invention may include creatine cyclohexyl ester. In another aspect, a composition made in accordance with the present invention includes creatine isopentyl ester. In still another aspect, the composition includes betaine cyclopentyl ester.

In another embodiment, a composition made in accordance with the present invention includes at least one of creatine hydrochloride, creatine mesylate, ethyl (α-guanido-methyl) ethanoate (Alpha-GEE), creatine ethyl ester hydrochloride, or combinations thereof. For example, the compositions may include creatine hydrochloride. In another aspect, the compositions of the present invention include ethyl (α-guanido-methyl) ethanoate. Without being bound to any particular theory, the presence of ethyl (α-guanido-methyl) ethanoate in the compositions of the invention (based on at least one antiviral therapeutic compound) provides an additional benefit of prevention and/or treatment for inflammation (along with the previously discussed benefits including boosting anti-viral immune activity). In particular, it is thought the hyper/systemic inflammation that accompanies severe cases of coronavirus can be prevented/controlled with a composition that includes ethyl (α-guanido-methyl) ethanoate alone or, as discussed in more detail below, with at least one other antiviral therapeutic compound disclosed herein.

Antiviral therapeutic compositions made in accordance with the present invention may include more than one of the above-mentioned antiviral therapeutic compounds. For example, the compositions of the invention may include two of the antiviral therapeutic compounds, e.g., creatine cyclohexyl ester and creatine hydrochloride, creatine isopentyl ester and betaine cyclopentyl ester, and the like. In another embodiment, the compositions of the invention may include three of the antiviral therapeutic compounds of the invention, e.g., a composition including creatine hydrochloride, creatine cyclohexyl ester, and creatine glycerol laurate ester. In yet another embodiment, the compositions of the invention may include creatine cyclohexyl ester, creatine isopentyl ester, and creatine hydrochloride. In other words, when a composition is made in accordance with the present invention, it can include any combination of the antiviral therapeutic compounds of the invention disclosed herein.

In this aspect, a composition may include about 300 mg to about 1500 mg of a first antiviral therapeutic compound of the invention and about 300 mg to about 1500 mg of a second antiviral therapeutic compound per dose. In one embodiment, a composition may include about 300 mg to about 800 mg of a first antiviral therapeutic compound of the invention and about 350 mg to about 1200 mg of a second antiviral therapeutic compound per dose. In another embodiment, a composition may include about 500 mg to about 750 mg of a first antiviral therapeutic compound of the invention and about 400 mg to about 1200 mg of a second antiviral therapeutic compound per dose. In still another embodiment, a composition may include about 600 mg to about 750 mg of a first antiviral therapeutic compound of the invention and about 300 mg to about 500 mg of a second antiviral therapeutic compound. In yet another embodiment, a composition may include about 300 mg to about 1500 mg of a first antiviral therapeutic compound of the invention, about 300 mg to about 1500 mg of a second antiviral therapeutic compound, and about 300 mg to about 1500 mg of a third antiviral therapeutic compound per dose. For example, a composition may include about 300 mg to about 400 mg of a first antiviral therapeutic compound of the invention, about 900 mg to about 1200 mg of a second antiviral therapeutic compound, and about 150 mg to about 300 mg of a third antiviral therapeutic compound per dose.

Moreover, the addition of other components may further enhance such compositions whether they include one or more of the antiviral therapeutic compounds of the invention. For example, proteins, amino acid supplements, complex carbohydrates, D-ribose, fats, fibers, or combinations thereof may be included in the compositions of the invention along with the at least one of the antiviral therapeutic compounds shown and discussed above. One such amino acid is glutamine—an α-amino acid found in the blood and muscle cells and considered a conditionally essential amino acid—maintains immune function by serving as the principle metabolic fuel for cells, acts as a precursor for protein synthesis, and along with cysteine and glycine, is involved in glutathione (GSH) synthesis. It also plays a supportive role during biochemical stress and sepsis. Thus, when the body is under stress, such as during intense exercise or illness, glutamine levels deplete, and more glutamine will be required by the body.

In one embodiment, the compositions of the invention may include glutamine or a salt thereof along with at least one of the antiviral therapeutic compounds discussed above. In this aspect, the compositions of the invention may include at least one antiviral therapeutic compound and a glutamine or glutamine salt. In another embodiment, the composition of the invention includes at least one antiviral therapeutic compound and a glutamine salt. In particular, it is contemplated that the composition of the invention includes at least one antiviral therapeutic compound and a glutamine salt that has a solubility of at least about 4 times greater than L-glutamine. In one embodiment, the composition of the invention includes at least one antiviral therapeutic compound and a glutamine salt that has a solubility of at least about 5 times greater than L-glutamine. In another embodiment, the composition of the invention includes at least one antiviral therapeutic compound and a glutamine salt that has a solubility of at least about 6 times greater than L-glutamine. In yet another embodiment, the composition of the invention includes at least one antiviral therapeutic compound and glutamine hydrochloride ($C_5H_{11}ClN_2O_3$) as generally represented by the formula below:

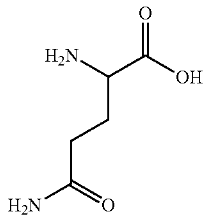

HCl

Without being bound by any particular theory, glutamine hydrochloride confers the additional benefit of increased solubility over L-glutamine and other forms of glutamine.

The compositions of the present invention may also include other forms of creatine including, but not limited to, creatine esters, creatine ethyl ester, creatine pyruvate, creatine phosphate, creatine alpha-ketoglutarate, creatine citrate, and combinations thereof along with at least one of the antiviral therapeutic compounds shown and discussed above. In this aspect, the compositions of the invention may include at least one antiviral therapeutic compound and a creatine ethyl ester, creatine ethyl ester salt, or a combination thereof. In one embodiment, the compositions of the invention include at least one antiviral therapeutic compound and creatine pyruvate. In another embodiment, the compositions of the invention include at least one antiviral therapeutic compound and creatine phosphate. In yet another embodiment, the compositions of the invention include at least one antiviral therapeutic compound and creatine alpha-ketoglutarate. In still another embodiment, the compositions of the invention include at least one antiviral therapeutic compound and creatine citrate. In yet another embodiment, the compositions of the invention include at least one antiviral therapeutic compound and at least two other forms of creatine as discussed above.

In another embodiment, the compositions of the present invention include at least one of the following: homeopathic antiviral therapeutic compounds, co-medications, nutraceuticals, plant extracts, herbal preparations including, cosmetic agents, or combinations thereof. In addition, the compositions of the invention may include vitamins such as vitamins C, D, and E.

The compositions of the present invention may further include at least one of any suitable auxiliaries including, but not limited to, diluents, binders, stabilizers, buffers, salts, lipophilic solvents, preservatives, adjuvants or the like. Pharmaceutically acceptable auxiliaries are preferred. Pharmaceutically acceptable carriers may be routinely selected that are suitable for the mode of administration, solubility and/or stability of the antiviral therapeutic compound.

Pharmaceutical excipients and additives useful in the present invention may also include, but are not limited to, proteins, peptides, amino acids, lipids, and carbohydrates. Suitable protein excipients include serum albumin such as human serum albumin (HSA), recombinant human albumin (rHA), gelatin, casein, and combinations thereof. Suitable amino acid components include, but are not limited to alanine, glycine, arginine, betaine, histidine, glutamic acid, aspartic acid, cysteine, lysine, leucine, isoleucine, valine, methionine, phenylalanine, aspartame, and combinations thereof. Suitable carbohydrate excipients include, but are not limited to monosaccharides such as fructose, maltose, galactose, glucose, D-mannose, sorbose, and combinations thereof; disaccharides, such as lactose, sucrose, trehalose, cellobiose, and combinations thereof; polysaccharides, such as raffinose, melezitose, maltodextrins, dextrans, starches, and combinations thereof; and alditols, such as mannitol, xylitol, maltitol, lactitol, xylitol, sorbitol (glucitol), myoinositol, and combinations thereof.

The composition may also contain pharmaceutically acceptable carriers such as coloring agents, emulsifying agents, suspending agents, ethanol, EDTA or similar chelating agents, citrate buffer, water, and combinations thereof. Moreover, the compositions may include polymeric excipients/additives such as polyvinylpyrrolidones, ficolls, dextrates, polyethylene glycols, flavoring agents, anti-microbial agents, sweeteners, antioxidants, anti-static agents, surfactants, lipids, steroids, and chelating agents.

In addition, the compositions may also include a buffer or a pH adjusting agent. Suitable buffers include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

The compositions of the invention include an effective amount of at least one antiviral therapeutic compound of the invention of about 40 percent by weight to about 100 percent by weight of the composition. As used herein, the term "effective amount" refers to an amount of the antiviral therapeutic compound necessary or sufficient to elicit the desired biological or medical response, including the amount of a compound that, when administered to a subject for treating a disease or condition, is sufficient to affect such treatment for the disease. The effective amount will vary depending on the particular antiviral therapeutic compound, and characteristics of the subject to be treated, such as age, weight, etc. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved.

In one embodiment, an effective amount of the at least one antiviral therapeutic compound in the composition ranges from about 50 percent by weight to about 100 percent by weight of the composition. In another embodiment, an effective amount of the at least one antiviral therapeutic compound in the composition ranges from about 60 percent by weight to about 100 percent by weight of the composition. In yet another embodiment, an effective amount of the at least one antiviral therapeutic compound in the composition ranges from about 70 percent by weight to about 100 percent by weight of the composition. In still another embodiment, an effective amount of the at least one antiviral therapeutic compound in the composition ranges from about 80 percent by weight to about 100 percent by weight of the composition.

In this aspect, the compositions of the invention may include an effective amount of at least one antiviral therapeutic compound of about 200 mg/g to about 1000 mg/g per dose. In another embodiment, the effective amount of at least one antiviral therapeutic ranges from about 300 mg/g to about 1000 mg/g per dose. In still another embodiment, the effective amount of at least one antiviral therapeutic compound ranges from about 500 mg/g to about 1000 mg/g per dose.

An effective dose may include the about 500 mg to about 1500 mg per 100 pounds body weight of the antiviral therapeutic compound(s). For example, in one embodiment, the effective dose may be from about 1500 mg to about 3000 mg of the antiviral therapeutic compound(s) for a subject that weighs up to 250 pounds. In one embodiment, the effective dose of the antiviral therapeutic compound(s) is from about 2250 mg to about 4500 mg for a subject that weighs over 250 pounds. In another embodiment, the effective dose of the antiviral therapeutic compound(s) is from about 750 mg to about 1500 mg per 100 pounds body weight. Depending on the method of administration (discussed in greater detail below), strength of the patient's immune system, and/or components of the composition, the effective dose may be administered once per day or more than one time per day.

Methods of Administration

The compositions may be administered to and used for preventing infection with coronavirus or influenza virus. In addition, compositions including the antiviral therapeutic compounds of the invention may be used for treating a patient infected with a strain of coronavirus or influenza virus. A "patient" may include humans and non-humans such as canines, pets, and farm animals. More specifically, in one embodiment, the compositions of the invention may be administered to a patient infected with SARS-COV-2. In another embodiment, the compositions of the invention may be administered to a patient infected with SARS. In yet another embodiment, the compositions of the invention may be administered to a patient infected with influenza virus. In still another embodiment, the compositions of the invention may be used prophylactically to prevent infection with coronavirus. In yet another embodiment, the compositions of the invention may be used prophylactically to prevent infection with influenza virus.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

The terms "prevention", "prevent", and "preventing" as used herein refer to a course of action (such as administering an antiviral therapeutic compound or related composition of the present invention) initiated prior to the onset of a clinical manifestation of infection or condition so as to prevent or reduce such clinical manifestation of the infection or condition. Such preventing need not be absolute to be useful.

A dose comprising an effective amount of the antiviral therapeutic compound may be administered once or twice daily. In another embodiment, the effective amount of the antiviral therapeutic compound may be administered multiple doses in a day, e.g., two to four doses. For example, in one embodiment, an effective amount of the antiviral compound may be administered in three separate doses per day. In another embodiment, an effective amount of the antiviral compound may be administered in four separate doses per day. In this aspect, if the daily effective amount is from about 500 mg to about 1500 mg of the antiviral therapeutic compound(s) per 100 pounds of body weight, a patient up to 250 pounds may receive about 1500 mg to about 3000 mg of the antiviral therapeutic compound(s) in a single daily dose or receive about 750 mg to about 1500 mg of the antiviral therapeutic compound(s) in two separate doses in the same day. In another embodiment, if the daily effective amount is from about 500 to about 1500 mg of the antiviral therapeutic compound(s) per 100 pounds of body weight, a patient up to 250 pounds may receive about 500 mg to 1000 mg of the antiviral therapeutic compound(s) in three separate doses in the same day. In yet another embodiment, if the daily effective amount is from about 500 to about 1500 mg of the antiviral therapeutic compound(s) per 100 pounds of body weight, a patient up to 250 pounds may receive about 375 mg to 750 mg of the antiviral therapeutic compound(s) in four separate doses in the same day.

The methods of administration of the composition described herein to the patient may vary. However, in one embodiment, the composition of the invention is administered to the patient intravenously. In fact, intravenous administration is particularly suitable for those antiviral therapeutic compounds of the present invention that have high solubility, e.g., creatine isopentyl ester, betaine cyclopentyl ester, creatine amide ethyl ester, creatine amide tert butyl ester, dicreatine glycerol ester, tricreatine glycerol ester, creatine hydrochloride, creatine mesylate, Alpha-GEE, creatine ethyl ester hydrochloride, and combinations thereof. Similarly, intravenous administration is suitable when the composition of the present invention is co-administered with other immunotherapies and antivirals (discussed in more detail below) that are already administered intravenously. In one embodiment, the composition of the invention is administered to a patient infected with coronavirus intravenously for up to 5 days. In another embodiment, the composition of the invention is administered to a patient infected with coronavirus intravenously for up to 10 days. In another embodiment, the composition of the invention is administered to a patient infected with coronavirus intravenously for up to 15 days.

In another embodiment, the composition of the present invention is administered to the patient orally. For example, the antiviral therapeutic composition may be encapsulated or tableted for a solid oral dosage form. In one embodiment, the antiviral therapeutic composition may be administered in the form of a pill, tablet, capsule, or gel capsule. In the alternative, the composition of the present invention may also be provided orally to the patient in a liquid, gel, or powder form. For example, the composition may be in the form of a powder suitable for mixing with water or other liquids. In this aspect, the composition may be added into a beverage or may be provided as an ingredient premixed in a beverage. The composition may also be administered as an elixir or as a solution formulation. In still another embodiment, the antiviral therapeutic composition may be administered in the form of a functional food, for example, a shake or bar. In yet another embodiment, the composition of the present invention is administered to the patient in the form of a nasal spray or nasal drops or nasal irrigation fluid or wash.

As used herein, "co-administration" includes administration of compositions disclosed herein before or after administration of unit dosages of one or more additional therapeutic agents, for example, administration of the composition disclosed herein within seconds, minutes, or hours of the administration of one or more additional therapeutic agents. For example, in some embodiments, the composition of the present invention is administered first, followed within seconds or minutes by administration of a unit dose of one or more additional therapeutic agents. Alternatively, in other embodiments, a unit dose of one or more additional therapeutic agents is administered first, followed by administration of the composition of the present invention. In some embodiments, the composition of the present invention is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of the composition of the present invention. Suitable doses of any co-administered compounds may optionally be lowered due to the combined action (e.g., additive or synergistic effects) of the compounds.

The composition of the invention may be used in connection with other types of immunotherapies, prodrugs, antivirals, and other adjunctive therapies. In fact, the compositions of the invention may be co-administered with immunotherapies such as monoclonal antibodies directed against key inflammatory cytokines such as interleukin-6 receptor (IL-6r) including, but not limited to, tocilizumab and sarilumab. In another embodiment, the compositions of the invention may be co-administered with prodrugs, antivirals and antiretrovirals, such as remdesivir and favipiravir, umifenovir, and lopinavir/ritonavir, respectively. In addition, the compositions of the invention may be co-administered with protease inhibitors or integrase strand transfer inhibitors having SARS-COV-2 activity. In yet another embodiment, the composition of the invention may be co-administered with chloroquine or hydroxychloroquine. In still another embodiment, the compositions of the invention may be co-administered with corticosteroids. In yet another embodiment, the compositions of the invention may be co-administered with convalescent plasma, hyperimmune immunoglobulins, or combinations thereof.

Antiviral Effects

The antiviral therapeutic compounds of the invention (and compositions including the antiviral compounds of the invention) promote increased cytokine release in the presence of the viral proteins. More specifically, interferon gamma release from T cells exposed to a viral protein is increased when an antiviral therapeutic compound of the invention is present.

In this aspect, the presence of at least one antiviral therapeutic compound of the invention may increase the release of interferon gamma (human) (IFNg) by at least about 10 percent when T cells are exposed to 100 ng/ml to 1000 ng/ml of viral protein. In one embodiment, the presence of an antiviral therapeutic compound of the invention increases release of IFNg by about 20 percent to 75 percent (as compared to the release of IFNg in T cells exposed to 10 ng/ml to 1000 ng/ml of viral protein without any antiviral therapeutic compound). In another embodiment, the presence of an antiviral therapeutic compound of the invention increases release of IFNg by about 25 percent to 70 percent (as compared to the release of IFNg in T cells exposed to viral protein without any antiviral therapeutic compound). In yet another embodiment, the presence of an antiviral therapeutic compound of the invention increases release of IFNg by about 35 percent to 70 percent (as compared to the release of IFNg in T cells exposed to viral protein without any antiviral therapeutic compound).

For example, the presence of betaine cyclopentyl ester may increase the release of interferon gamma (human) (IFNg) by at least about 20 percent when T cells are exposed to 100 ng/ml to 1000 ng/ml of viral protein. In one embodiment, the presence of betaine cyclopentyl ester increases release of IFNg by about 20 percent to 70 percent (as compared to the release of IFNg in T cells exposed to 10 ng /ml to 1000 ng/ml of viral protein without any antiviral therapeutic compound). In another embodiment, the presence of a betaine cyclopentyl ester increases release of IFNg by about 30 percent to 60 percent (as compared to the release of IFNg in T cells exposed to viral protein without any antiviral therapeutic compound). In yet another embodiment, the presence of betaine cyclopentyl ester increases release of IFNg by about 35 percent to 55 percent (as compared to the release of IFNg in T cells exposed to viral protein without any antiviral therapeutic compound).

Similarly, the presence of creatine cyclohexyl ester may increase the release of interferon gamma (human) (IFNg) by at least about 20 percent when T cells are exposed to 100 ng/ml to 1000 ng/ml of viral protein. In one embodiment, the presence of creatine cyclohexyl ester increases release of IFNg by about 20 percent to 70 percent (as compared to the release of IFNg in T cells exposed to 10 ng /ml to 1000 ng/ml of viral protein without any antiviral therapeutic compound). In another embodiment, the presence of a creatine cyclohexyl ester increases release of IFNg by about 30 percent to 60 percent (as compared to the release of IFNg in T cells exposed to viral protein without any antiviral therapeutic compound). In yet another embodiment, the presence of creatine cyclohexyl ester increases release of IFNg by about 35 percent to 55 percent (as compared to the release of IFNg in T cells exposed to viral protein without any antiviral therapeutic compound).

Likewise, the presence of creatine isopentyl ester may increase the release of interferon gamma (human) (IFNg) by at least about 40 percent when T cells are exposed to 100 ng/ml to 1000 ng/ml of viral protein. In one embodiment, the presence of creatine cyclohexyl ester increases release of IFNg by about 40 percent to 75 percent (as compared to the release of IFNg in T cells exposed to 10 ng/ml to 1000 ng/ml of viral protein without any antiviral therapeutic compound). In another embodiment, the presence of a creatine isopentyl ester increases release of IFNg by about 45 percent to 70 percent (as compared to the release of IFNg in T cells exposed to viral protein without any antiviral therapeutic compound). In yet another embodiment, the presence of creatine isopentyl ester increases release of IFNg by about 60 percent to 70 percent (as compared to the release of IFNg in T cells exposed to viral protein without any antiviral therapeutic compound).

The antiviral compounds of the invention (and compositions including the antiviral compounds of the invention) also reduce the proinflammatory response that occurs in the presence of the viral proteins. More specifically, proinflammatory markers may have reduced expression in the presence of a viral protein when an antiviral compound of the invention is also present (as compared to the expression with no antiviral compound).

In this aspect, interleukin-6 (IL-6), a proinflammatory cytokine, may have at least about 10 percent reduced expression to a viral protein when an antiviral compound of the invention is present. In one embodiment, IL-6 has at least about 20 percent reduced expression to a viral protein when an antiviral compound of the invention is present. In another embodiment, the presence of the antiviral compound reduces expression of IL-6 when a viral protein is present by about 30 percent or more. In yet another embodiment, IL-6 has at least about 40 percent reduced expression to a viral protein when an antiviral compound of the invention is present. In still another embodiment, the presence of the antiviral compound reduces expression of IL-6 when a viral protein is present by about 60 percent or more.

Similarly, interleukin 1 beta (IL-1β), another proinflammatory cytokine, may have at least about 40 percent reduced expression to a viral protein when an antiviral compound of the invention is present. In one embodiment, IL-1β has at least about 50 percent reduced expression to a viral protein when an antiviral compound of the invention is present. In another embodiment, the presence of the antiviral compound reduces expression of IL-1β when a viral protein is present by about 60 percent or more. In yet another embodiment, IL-1β has at least about 70 percent reduced expression to a viral protein when an antiviral compound of the invention is present. In still another embodiment, the presence of the antiviral compound reduces expression of IL-1β when a viral protein is present by about 80 percent or more.

While TNF, another proinflammatory cytokine, may not experience much expression when in the presence of a viral protein, that expression may still be reduced when an antiviral compound of the invention is also present. For example, TNF may have at least about 5 percent reduced expression to a viral protein when an antiviral compound of the invention is present. In one embodiment, TNF has at least about 10 percent reduced expression to a viral protein when an antiviral compound of the invention is present. In another embodiment, the presence of the antiviral compound reduces expression of TNF when a viral protein is present by about 15 percent or more.

In this same aspect, CXCL1 and CXCL2, chemokines that attract inflammatory cells, may have at least about 20 percent reduced expression to a viral protein when an antiviral compound of the invention is present. In one embodiment, CXCL1 and/or CXCL2 have at least about 30 percent reduced expression to a viral protein when an antiviral compound of the invention is present. In another embodiment, the presence of the antiviral compound reduces expression of CXCL1 and/or CXCL2 when a viral protein is present by about 60 percent or more. In yet another embodiment, CXCL1 and/or CXCL2 have at least about 80 percent reduced expression to a viral protein when an antiviral compound of the invention is present. In still another embodiment, the presence of the antiviral compound reduces expression of CXCL1 and/or CXCL2 when a viral protein is present by about 80 percent or more.

EXAMPLES

The following non-limiting examples are merely illustrative of the preferred embodiments of the present invention, and are not to be construed as limiting the invention, the scope of which is defined by the appended claims.

Example 1: Solubility Determination

The saturated solubility of several antiviral therapeutic compounds of the present invention in deionized water was determined by adding increasing amounts to 5 ml of solvent in screw-capped glass bottles placed in a shaking water bath at 25° C. After 1.5 hour, the saturated solutions were vortexed and 2-ml aliquots removed and centrifuged in microcentrifuge tubes at 11,000 rpm for 5min. Concentrations were analyzed by HPLC by diluting 500 μL of supernatant with mobile phase (500 μL). The mean±standard deviation of the saturation solubility for each antiviral therapeutic compound is calculated from the corresponding standard curves.

As shown in Table 1 below, the solubility of betaine cyclopentyl ester, creatine amide ethyl ester, and creatine isopentyl ester is significantly higher than creatine monohydrate. While not shown, betaine cyclopentyl ester has an aqueous solubility significantly greater than betaine hydrochloride. And, while creatine cyclohexyl ester appears to have a solubility similar to creatine monohydrate, as discussed above, the lipophilicity of this compound may provide for better tissue and cell penetration. Without being bound by any particular theory, since the salt used in this particular creatine isopentyl ester, i.e., the tosylate, is not a particularly strong counter ion, the use of HCl or Br salts in place of the tosylate may result in higher solubility.

TABLE 1

| Aqueous Solubility Assessments | | | | | |
|---|---|---|---|---|---|
| | Control (Creatine Monohydrate) | Betaine Cyclopentyl Ester | Creatine Cyclohexyl Ester | Creatine Amide Ethyl Ester | Creatine Isopentyl Ester |
| MW (g/mol) | 149.7 | 266 | 385 | 233 | 238 |
| Solubility (mg/ml) | 21.0 ± 1.9 | >600 | 15-20 | >600 | >600 |
| Ratio (relative to CM) | 1.0 | >29 | 0.71 | >29 | >29 |

Example 2: Caco-2 Cell Permeability Assay

Caco-2 cells are seeded onto collagen-coated Transwell polycarbonate membrane inserts (12-mm diameter; 1-μm pore size) (Fisher Scientific, Mississauga, ON) at a density of 60,000 cells/$cm^2$. The cells are grown in DMEM supplemented with 10 percent fetal bovine serum and maintained in 5 percent $CO_2$ environment. Cells are cultured for a period of 18-21 days, after which confluent monolayers are used for permeability studies.

To evaluate the permeability of the antiviral therapeutic compounds, the culture media is removed from the cells and replaced with Tyrode's buffer consisting of 136-mM NaCl, 2.6-mM KCl, 1.8-mM $CaCl_2$, 1-mM $MgCl_{2,}$, 0.36-mM NaH2$PO_4$, 5.56-mM D-Glucose, and 5-mM HEPES at pH 7.4. After a 30-min pre-incubation period, Tyrode's buffer is removed from the apical compartment and replaced with 0.5 ml of Tyrode's buffer containing each of the antiviral therapeutic compounds (10 mM) (pH 7.4 and 37° C.). 50 μL samples are removed from the apical compartment at the start and conclusion of the permeability experiment. 100 μL samples are removed from the basolateral compartment at 0, 15, 30, 60, and 90 min. Passage from the apical to basolateral compartments is analyzed using HPLC. Permeability coefficients are determined based on the following equation:

$$P_{app} = \left( \frac{\frac{dQ}{dt}}{C_0 \times A} \right)$$

where dQ/dt is the rate of permeation of the antiviral therapeutic compound across the cells, Co is the donor concentration at time zero and A is the area of the cell monolayer.

Example 3: Antiviral Therapeutic Compositions

Several example compositions are provided below:

TABLE 2

| Example Compositions | | | | | | |
|---|---|---|---|---|---|---|
| Ingredient | Ex A | Ex B | Ex C | Ex D | Ex E | Ex F |
| Antiviral therapeutic Compound/Complex | 700 mg | 600 mg | 600 mg | 600 mg | 800 mg | 1000 mg |
| Alpha-GEE | 400 mg | 1200 mg | 1200 mg | — | — | — |
| Glutamine HCl | — | — | 2000 mg | 2000 mg | — | 2000 mg |
| Vitamin D | 25 mcg | — | — | | — | — |
| Calcium citrate | — | 100 mg | 100 mg | 100 mg | 100 mg | 100 mg |
| Magnesium glyconate | — | 10 mg | 10 mg | | — | — |
| Zinc citrate | 12 mg | | — | | — | — |
| Potassium chloride | — | 175 mg | 175 mg | 175 mg | 175 mg | 175 mg |
| Sodium chloride | — | 250 mg | 250 mg | 250 mg | — | — |

TABLE 2-continued

| Example Compositions | | | | | | |
|---|---|---|---|---|---|---|
| Ingredient | Ex A | Ex B | Ex C | Ex D | Ex E | Ex F |
| BCAA Complex | — | 5000 mg | 5000 mg | 5000 mg | — | — |
| Selenium | 30 mcg | — | — | — | — | — |
| Black Elderberry Extract | 150 mcg | — | — | — | — | — |
| Green Tea Extract | 50 mg | — | — | — | — | — |

The antiviral therapeutic compound may include one or more antiviral therapeutic compounds disclosed herein or one or more antiviral therapeutic compounds and another form of creatine,. Example A is administered once a day with a serving size of 2 capsules. Examples B-F are administered once a day by mixing one or two scoops with 8-12 ounces of water or other liquid suitable for ingestion.

Example 4: Effect of Compounds on Host Cell Inflammatory Response to SARS-COV-2 Proteins Calu-3 (human airway epithelial cell line) host cells were seeded onto collagen-coated Transwell polycarbonate membrane inserts (12-mm diameter; 1-μm pore size) (Fisher Scientific, Winnipeg, MB) at a density of 60,000 cells/$cm^2$. The cells were grown in DMEM supplemented with 10 percent fetal bovine serum and maintained in 5 percent $CO_2$ environment. Cells were grown to confluency, after which confluent monolayers were treated with 0.5 μg/ml of SARS-CoV-2 spike protein (SPK) or 0.5 μg/ml of SARS-COV-2 nuclear capsid protein (NUC) with or without 320 μM of certain antiviral compounds of the present invention.

Cells were collected and prepared for gene expression of IL6, IL1-β, TNF, CXCL-1, and CXCL-2 using qRT-PCR.

As shown in FIG. 1, the expression of the proinflammatory cytokine IL-6 after exposure to SPK when none of the antiviral therapeutic compounds of the invention are present is about 140 percent over that of the media control. The presence of Alpha-GEE and creatine hydrochloride reduce the expression of IL-6 in Calu-3 cells by about 40 percent and 50 percent, respectively (as compared to the expression of IL-6 when no antiviral therapeutic compounds of the invention are present). The presence of creatine cyclohexyl ester (V07) and creatine isopentyl ester (V09) reduces the expression by about 100 percent and 90 percent, respectively (as compared to the expression of IL-6 when no antiviral therapeutic compounds of the invention are present). In other words, the expression of IL-6 after 24-hr exposure to the spike protein in the presence of creatine cyclohexyl ester (V07) is less than about 30 percent of the expression when no antiviral therapeutic compound of the present invention is present. Similarly, expression of IL-6 after 24-hr exposure to the spike protein in the presence of creatine isopentyl ester (V09) is less than about 35 percent of the expression when no antiviral therapeutic compound of the present invention is present.

The expression of the proinflammatory cytokine IL-1β after exposure to SPK when none of the antiviral therapeutic compounds of the invention are present is about 120 percent over that of the media control. The presence of Alpha-GEE and creatine hydrochloride reduce the expression of IL-1β in Calu-3 cells by about 75 percent and 50 percent, respectively (as compared to the expression of IL-1β when no antiviral therapeutic compounds of the invention are present). The presence of betaine cyclopentyl ester (V05), creatine cyclohexyl ester (V07) and creatine isopentyl ester (V09) reduces the expression by about 50 percent, 100 percent, and 80 percent, respectively (as compared to the expression of IL-1β when no antiviral therapeutic compounds of the invention are present). In other words, the expression of IL-1β after 24-hr exposure to the spike protein in the presence of creatine hydrochloride and betaine cyclopentyl ester (V05) is less than about 60 percent of the expression when no antiviral therapeutic compound of the present invention is present. Similarly, expression of IL-1β after 24-hr exposure to the spike protein in the presence of creatine cyclohexyl ester (V07) is less than about 20 percent of the expression when no antiviral therapeutic compound of the present invention is present. Likewise, expression of IL-1β after 24-hr exposure to the spike protein in the presence of creatine isopentyl ester (V09) is less than about 35 percent of the expression when no antiviral therapeutic compound of the present invention is present.

The expression of the proinflammatory cytokine TNF after exposure to SPK when none of the antiviral therapeutic compounds of the invention are present is only about 40 percent over that of the media control. While creatine hydrochloride and betaine cyclopentyl ester (V05) slightly reduces the expression of TNF in Calu-3 cells (as compared to the expression of TNF when no antiviral therapeutic compounds of the invention are present), the presence of creatine cyclohexyl ester (V07) and creatine isopentyl ester (V09) reduces the expression by about 30 percent and 20 percent, respectively (as compared to the expression of TNF when no antiviral therapeutic compounds of the invention are present). In other words, the expression of TNF after 24-hr exposure to the spike protein in the presence of creatine cyclohexyl ester (V07) and creatine isopentyl ester (V09) is less than about 50 percent of the expression when no antiviral therapeutic compound of the present invention is present. In fact, the expression of TNF after 24-hr exposure to the spike protein in the presence of creatine cyclohexyl ester (V07) is less than about 30 percent of the expression when no antiviral therapeutic compound of the present invention is present.

The expression of CXCL1 and CXCL2 after exposure to SPK when no antiviral therapeutic compounds are present is about 120 and 140 percent, respectively. Alpha-GEE reduces this expression by about 60 percent and 70 percent, respectively (as compared to the expression of CXCL1 and CXCL2 when no antiviral therapeutic compounds of the invention are present). Creatine hydrochloride reduces the expression of CXCL1 by about 40 percent. Betaine cyclopentyl ester reduces the expression of CXCL1 and CXCL2 by about 30 percent and 50 percent, respectively (as compared to the expression of CXCL1 and CXCL2 when no antiviral therapeutic compounds of the invention are present). As with the other genes that were examined, the most profound reduction in the expression of CXCL1 and CXCL2 occurred in the presence of creatine cyclohexyl ester (V07)

and creatine isopentyl ester (V09). In particular, in the presence of creatine cyclohexyl ester (V07) or creatine isopentyl ester (V09), expression of CXCL1 was less than about 25 percent of the expression of CXCL1 or CXCL2 when no antiviral therapeutic compounds of the invention were present.

Figure 2:
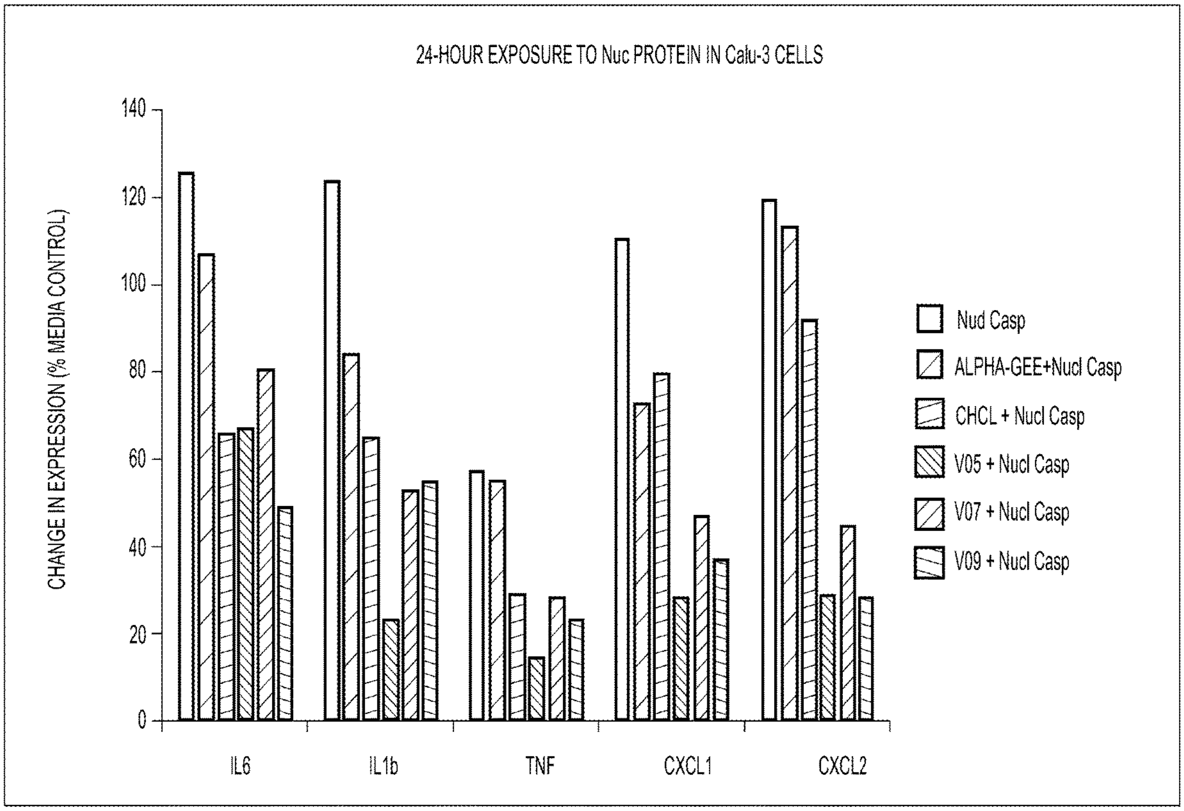
FIG. 2 is a graphical illustration showing the expression of inflammatory genes in response to exposure to SARS-COV-2 nuclear capsid protein in the presence and absence of certain antiviral therapeutic compounds of the present disclosure.

As shown in FIG. 2, the expression of the proinflammatory cytokine IL-6 after exposure to NUC when none of the antiviral therapeutic compounds of the invention are present is about 125 percent over that of the media control. The presence of Alpha-GEE reduce the expression of IL-6 in Calu-3 cells by about 20 percent (as compared to the expression of IL-6 when no antiviral therapeutic compounds of the invention are present). The presence of creatine hydrochloride and betaine cyclopentyl ester (V05) reduces the expression by about 60 percent (as compared to the expression of IL-6 when no antiviral therapeutic compounds of the invention are present). The presence of creatine cyclohexyl ester (V07) and creatine isopentyl ester (V09) reduces the expression by about 45 percent and 75 percent, respectively (as compared to the expression of IL-6 when no antiviral therapeutic compounds of the invention are present). In other words, the expression of IL-6 after 24-hr exposure to the NUC protein in the presence of betaine cyclopentyl ester (V07) is less than about 55 percent of the expression when no antiviral therapeutic compound of the present invention is present. Similarly, expression of IL-6 after 24-hr exposure to the NUC protein in the presence of creatine isopentyl ester (V09) is about 40 percent or less of the expression when no antiviral therapeutic compound of the present invention is present.

The expression of the proinflammatory cytokine IL-1β after exposure to NUC when none of the antiviral therapeutic compounds of the invention are present is about 120 percent over that of the media control. The presence of Alpha-GEE and creatine hydrochloride reduce the expression of IL-1β in Calu-3 cells by about 40 percent and 55 percent, respectively (as compared to the expression of IL-1β when no antiviral therapeutic compounds of the invention are present). The presence of betaine cyclopentyl ester (V05), creatine cyclohexyl ester (V07) and creatine isopentyl ester (V09) reduces the expression by about 100 percent, 70 percent, and 70 percent, respectively (as compared to the expression of IL-1β when no antiviral therapeutic compounds of the invention are present). In other words, the expression of IL-1β after 24-hr exposure to the NUC protein in the presence of betaine cyclopentyl ester (V05) is less than about 20 percent of the expression when no antiviral therapeutic compound of the present invention is present. Similarly, expression of IL-1β after 24-hr exposure to the NUC protein in the presence of creatine cyclohexyl ester (V07) and creatine isopentyl ester (V09) is less than about 45 percent of the expression when no antiviral therapeutic compound of the present invention is present.

The expression of the proinflammatory cytokine TNF when none of the antiviral therapeutic compounds of the invention are present is less than about 60 percent over that of the media control. Creatine hydrochloride, creatine cyclohexyl ester and creatine isopentyl ester reduce the expression of TNF in Calu-3 cells by about 25 percent (as compared to the expression of TNF when no antiviral therapeutic compounds of the invention are present). Betaine cyclopentyl ester reduces the expression of TNF in Calu-3 cells by about 45 percent (as compared to the expression of TNF when no antiviral therapeutic compounds of the invention are present). In other words, the expression of TNF after 24-hr exposure to the NUC protein in the presence of betaine cyclopentyl ester (V05) is less than about 20 percent of the expression when no antiviral therapeutic compound of the present invention is present. Similarly, expression of TNF after 24-hr exposure to the NUC protein in the presence of creatine cyclohexyl ester (V07) and creatine isopentyl ester (V09) is less than about 35 percent of the expression when no antiviral therapeutic compound of the present invention is present.

The expression of CXCL 1 and CXCL2 when no antiviral therapeutic compounds are present is about 110 and 120 percent, respectively. Alpha-GEE and creatine hydrochloride reduces the expression of CXCL1 by about 30 percent (as compared to the expression of CXCL1 when no antiviral therapeutic compounds of the invention are present). Creatine hydrochloride reduces the expression of CXCL2 by about 25 to 30 percent. Betaine cyclopentyl ester reduces the expression of CXCL1 and CXCL2 by about 85 percent and 95 percent, respectively (as compared to the expression of CXCL1 and CXCL2 when no antiviral therapeutic compounds of the invention are present). In the presence of creatine cyclohexyl ester (V07) or creatine isopentyl ester (V09), expression of CXCL1 and CXCL2 reduced by at least about 60-70 percent (as compared to the expression of CXCL1 and CXCL2 when no antiviral therapeutic compounds of the invention are present).

Example 5: Effect of Compounds on T-cell Response to Spike Peptide

To evaluate the effect of the antiviral therapeutic compounds on T-cells, 40,000 T cells were plated in a 96-well plate in the presence of 40,000 T2 cells (a B-LCL expressing HLA-A*0201). The cells were exposed to media, increasing concentrations of KLPDDFTGCV, a peptide that corresponds to the Spike protein (position 424-433) of the novel coronavirus SARS-CoV-2, and certain antiviral therapeutic compounds of the invention. More specifically, Alpha-GEE, creatine hydrochloride, betaine cyclopentyl ester (V05), creatine cyclohexyl ester (V07), and creatine isopentyl ester (V09) were examined.

Figure 3A:
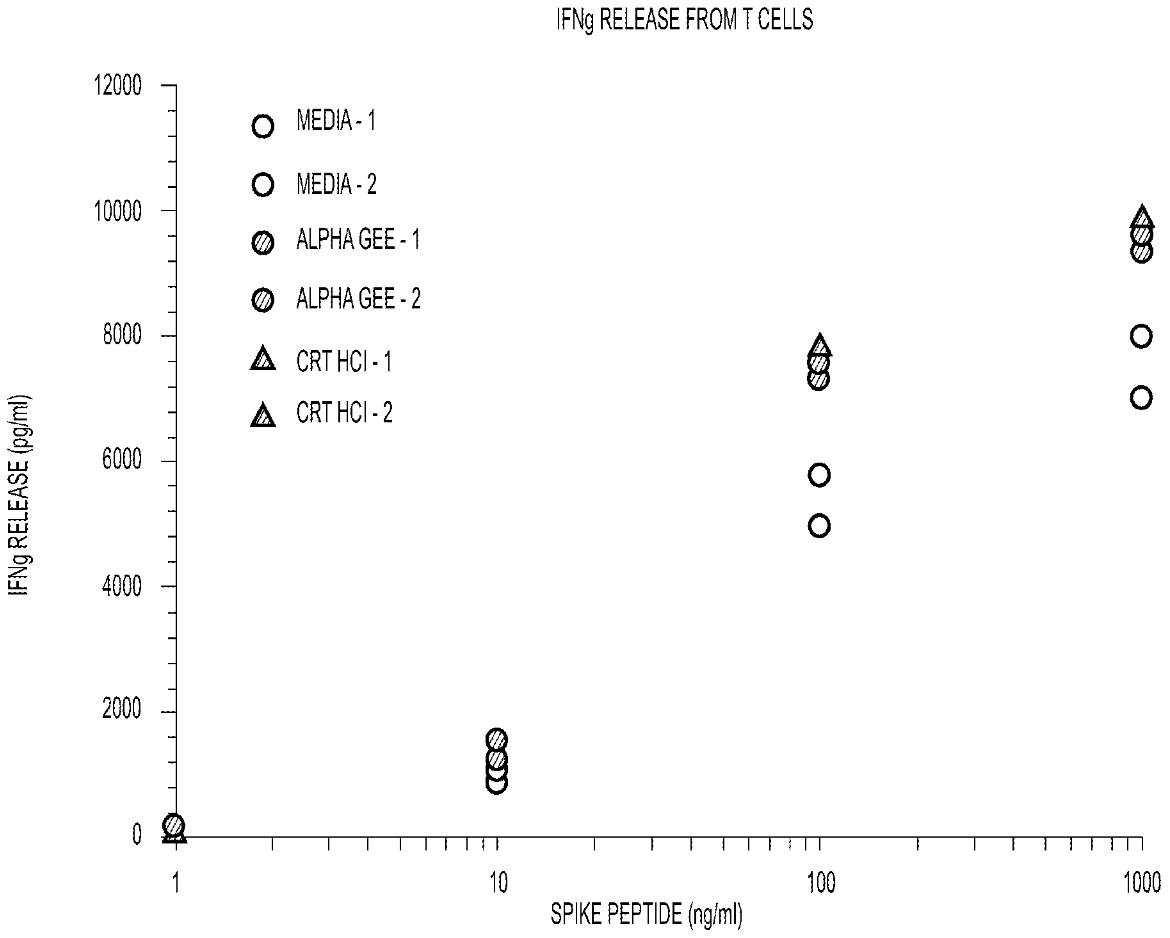
FIGS. 3A-3B are graphical illustrations showing cytokine release following antigen challenge in SARS-COV-2 T cells in the presence and absence of certain antiviral therapeutic compounds of the present disclosure.
Figure 3B:
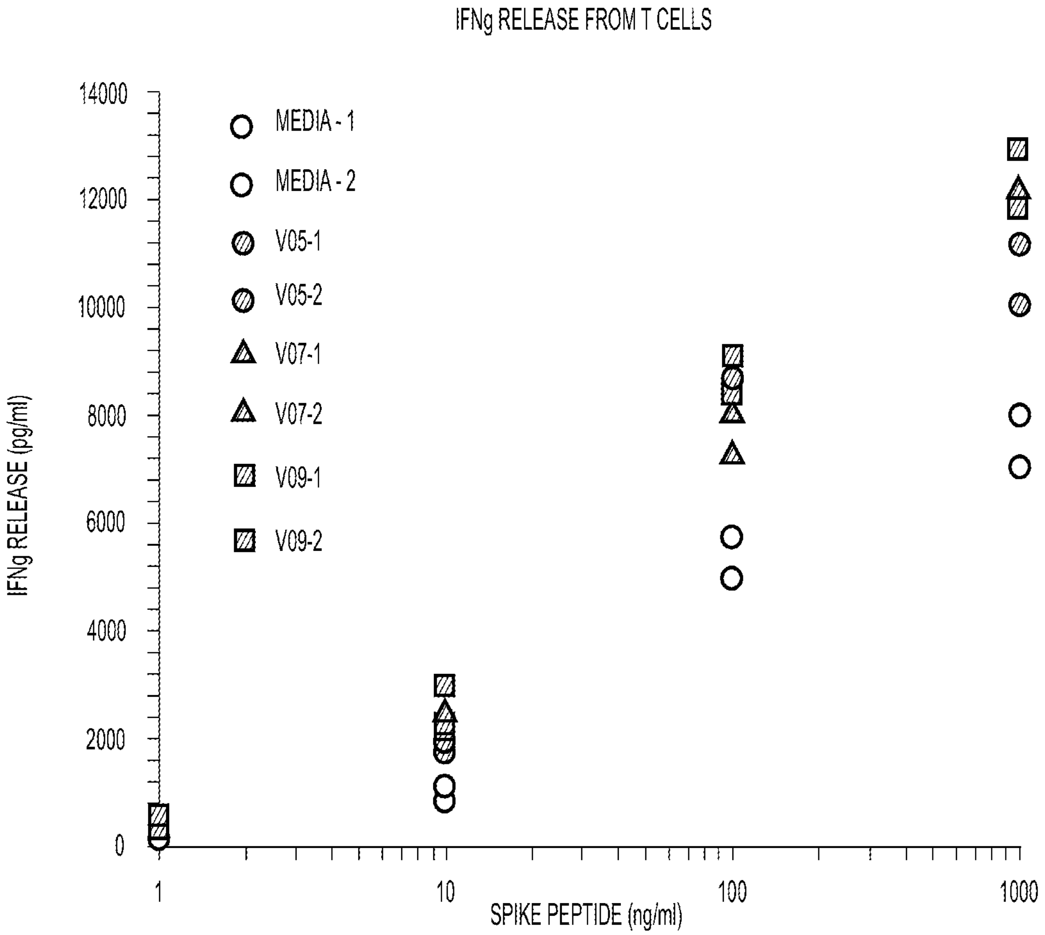

FIGS. 3A and 3B show that release of IFNg from T cells in the presence of Alpha-GEE, creatine hydrochloride, betaine cyclopentyl ester (V05), creatine cyclohexyl ester (V07), and creatine isopentyl ester (V09) was increased over the control (media alone without any antiviral therapeutic compounds of the invention).

Although the present invention has been described with reference to particular embodiments, it will be understood to those skilled in the art that the invention is capable of a variety of alternative embodiments within the spirit of the appended claims. For example, the present invention is also contemplated for use prophylactically as a preventative or as treatment or support for treatment of cold viruses.

What is claimed is:

1. A method of reducing inflammatory response to viral proteins in a patient in need thereof, comprising:

administering to the patient an effective amount of a composition comprising at least one antiviral therapeutic compound, wherein the antiviral therapeutic compound is selected from the group consisting of creatine cyclohexyl ester, creatine isopentyl ester, betaine cyclopentyl ester, and combinations thereof.

2. The method of claim 1, wherein the antiviral therapeutic compound is present in the composition in an amount of about 50 percent or greater by weight of the composition.

3. The method of claim 2, wherein the composition is administered to the patient orally.

4. The method of claim 2, wherein the composition is administered to the patient intravenously.

5. The method of claim 1, wherein the step of administering decreases expression of proinflammatory cytokines in the patient.

6. The method of claim 1, wherein the step of administering increases interferon gamma release in the patient.

7. A method of reducing inflammatory response to viral proteins in a patient in need thereof, comprising:

administering to the patient an effective amount of at least one antiviral therapeutic compound, wherein the antiviral therapeutic compound is selected from the group consisting of creatine cyclohexyl ester, creatine isopentyl ester, betaine cyclopentyl ester, and combinations thereof.

8. The method of claim 7, wherein the step of administering comprises administering the antiviral therapeutic compound in an amount of about 400 mg/g to about 500 mg/g per dose.

9. The method of claim 7, wherein the step of administering comprises administering the antiviral therapeutic compound to the patient orally.

10. The method of claim 7, wherein the step of administering comprises administering the antiviral therapeutic compound to the patient intravenously.

11. The method of claim 7, wherein the step of administering decreases expression of proinflammatory cytokines in the patient.

12. The method of claim 7, wherein the step of administering increases interferon gamma release in the patient.

13. A method of reducing inflammatory response to viral proteins in a patient in need thereof, comprising:

administering to the patient an effective amount of a composition comprising at least one antiviral therapeutic compound and at least one anti-inflammatory agent, wherein the antiviral therapeutic compound is selected from the group consisting of creatine cyclohexyl ester, creatine isopentyl ester, betaine cyclopentyl ester, and a combination thereof and wherein the anti-inflammatory agent comprises ethyl (α-guanido-methyl) ethanoate, wherein the antiviral therapeutic compound is present in the composition in an amount of about 50 percent or greater by weight of the composition.

14. The method of claim 13, wherein the composition is administered to the patient orally.

15. The method of claim 13, wherein the composition is administered to the patient intravenously.

16. The method of claim 13, wherein the composition comprises about 400 mg to about 800 mg of the antiviral therapeutic compound per dose and about 300 mg to about 600 mg of the anti-inflammatory agent per dose.

17. The method of claim 13, wherein the step of administering decreases expression of proinflammatory cytokines in the patient.

18. The method of claim 13, wherein the step of administering increases interferon gamma release in the patient.

19. The method of claim 1, wherein the patient is infected with coronavirus, influenza virus, or both.

20. The method of claim 1, wherein antiviral therapeutic compound is selected from the group consisting of creatine cyclohexyl ester, creatine isopentyl ester, and combinations thereof.

21. The method of claim 7, wherein antiviral therapeutic compound is selected from the group consisting of creatine cyclohexyl ester, creatine isopentyl ester, and combinations thereof.

22. The method of claim 13, wherein antiviral therapeutic compound is selected from the group consisting of creatine cyclohexyl ester, creatine isopentyl ester, and combinations thereof.

* * * * *